(12) United States Patent
Khankari et al.

US006221392B1

(10) Patent No.: US 6,221,392 B1
(45) Date of Patent: Apr. 24, 2001

(54) RAPIDLY DISSOLVING ROBUST DOSAGE FORM

(75) Inventors: Rajendra K. Khankari, Maple Grove; John Hontz, Plymouth; Sara J. Chastain, Maple Grove; Leo Katzner, Eden Prairie, all of MN (US)

(73) Assignee: Cima Labs Inc., Eden Prairie, MN (US)

( * ) Notice: Subject to any disclaimer, the term of this patent is extended or adjusted under 35 U.S.C. 154(b) by 0 days.

(21) Appl. No.: 09/464,882

(22) Filed: Dec. 16, 1999

Related U.S. Application Data

(63) Continuation of application No. 09/388,803, filed on Sep. 2, 1999, now abandoned, which is a continuation of application No. 09/057,884, filed on Apr. 9, 1998, now Pat. No. 6,024,981.
(60) Provisional application No. 60/043,242, filed on Apr. 16, 1997.

(51) Int. Cl.$^7$ ...................................................... A61K 9/20
(52) U.S. Cl. .................... 424/464; 424/435; 424/441; 424/465; 424/469; 424/484
(58) Field of Search .................... 424/494, 490, 424/497, 465, 469, 464, 441, 439, 484, 435

(56) References Cited

U.S. PATENT DOCUMENTS

| 3,962,417 | 6/1976 | Howell | 424/52 |
|---|---|---|---|
| 4,613,497 | 9/1986 | Chavkin | 424/44 |
| 4,639,368 | 1/1987 | Niazi et al. | 424/48 |
| 4,687,662 | 8/1987 | Schobel | 424/44 |
| 4,753,792 | 6/1988 | Aberg | 424/44 |
| 4,940,588 | 7/1990 | Sparks et al. | 424/490 |
| 5,055,306 | 10/1991 | Barry et al. | 424/482 |
| 5,178,878 | 1/1993 | Wheling et al. | 424/466 |
| 5,225,197 | 7/1993 | Bolt et al. | 424/440 |
| 5,464,632 | 11/1995 | Cousin et al. | 424/465 |
| 5,536,526 | 7/1996 | Virtanen et al. | 426/658 |
| 5,607,697 | 3/1997 | Alkire et al. | 424/495 |
| 5,876,759 | * 3/1999 | Gowan, Jr. | 424/494 |
| 6,024,981 | * 2/2000 | Khankari et al. | 424/464 |

OTHER PUBLICATIONS

U.S. Pharmacopoeia No. 23, 1995, Chap. 1216, "Tablet Friability".

Non–Certified Copy of the complete file history of U.S. Patent No. 5,876,759, Mar. 2, 1999 to Gowan, Jr.

\* cited by examiner

*Primary Examiner*—James M. Spear
(74) *Attorney, Agent, or Firm*—Lerner, David, Littenberg, Krumholz & Mentlik, LLP

(57) ABSTRACT

The invention is directed to a hard tablet that can be stored, packaged and processed in bulk. Yet the tablet dissolves rapidly in the mouth of the patient with a minimum of grit. The tablet is created from an active ingredient mixed into a matrix of a nondirect compression filler and a relatively high lubricant content.

1 Claim, No Drawings

RAPIDLY DISSOLVING ROBUST DOSAGE FORM

CROSS REFERENCE TO RELATED APPLICATIONS

The present application is a continuation of U.S. patent application Ser. No. 09/388,803 filed Sep. 2, 1999 ABANDONED, which is a continuation of U.S. patent application Ser. No. 09/057,884 filed Apr. 9, 1998 U.S. Pat. No. 6,024,981, which in turn claims benefit of U.S. Provisional Patent Application Ser. No. 60/043,242, filed on Apr. 16, 1997, the disclosures of which are hereby incorporated by reference herein.

FIELD OF THE INVENTION

The present invention relates to the pharmaceutical industry, the medical industry, and, in particular, to the creation of dosage forms.

BACKGROUND OF THE INVENTION

It is known to produce an in-mouth disintegrable dosage form for the delivery of drugs. In fact, patents relating generally to this area date back to the last century. Such tablets have significant advantages over other dosage forms; particularly for those who cannot, or will not, swallow a tablet or capsule. Solid dosage forms are far more convenient than liquids. However, the design of orally disintegrable dosage forms carries with it its own set of unique problems.

Chewable tablets such as, for example, those disclosed in U.S. Pat. No. 5,225,197 to Bolt, can be provided. However, such dosage forms often provide inadequate taste-masking of bad tasting medicaments. Chewable formulations are also often incompatible with, for example, delicate microparticles or time-released microparticles. The compressive force used in forming tablets and/or during chewing will often rupture such structures either exposing the patient to the objectionable taste of the material contained therein, or interfering with the structural integrity of the encapsulant and thereby altering its drug delivery profile.

Non-chewable dosage forms have also been tried. For example, Cima Labs has produced oral dosage forms including microparticles and effervescents which rapidly disintegrate in the mouth and provide adequate taste-masking. See Wehling et al., U.S. Pat. No. 5,178,878. Zydis, on the other hand, produces a rapidly dissolvable, freeze-dried, sugar matrix to produce a rapidly dissolving tablet. While these dosage forms are effective, they provide significant problems in terms of production, storage, transport and during consumer usage. They are also significantly more costly to produce.

According to U.S. Pharmacopoeia No. 23, 1995, Chap. 1216 entitled "Tablet Friability," the text of which is hereby incorporated by reference, effervescent tablets and chewable tablets often have different specifications as far as friability, when compared to normal tablets. These tablets normally require special packaging. That, however, is a great understatement.

The Zydis tablets, for example, are so fragile that the matrix material must be formed by freeze-drying in an individual tablet-sized container. While the use of an effervescent couple in combination with microparticles as disclosed in Wheling et al. does overcome the need for such extreme measures, the need to minimize in-mouth disintegration times still require the use of nontraditional packaging and processing methodology. For example, normal conveyors such as vibratory conveyors or bulk hoppers common in the pharmaceutical industry could not be used, as these high-speed, high-volume devices tend to cause damage to the resulting tablets. Similarly, the resulting tablets cannot be stored on a hopper after tableting but before packaging. This can seriously interfere with the processing efficiencies of high-volume presses.

Moreover, the resulting tablets have to be packaged in individual, blister-type packages that are robust enough to avoid tablet breakage. They could not be packaged in a conventional, multi-tablet bottle, individual foil pouches or traditional blister packaging.

SUMMARY OF THE INVENTION

The present invention relates to a hard, compressed, rapidly dissolvable dosage form adapted for direct oral dosing. The dosage form includes an active ingredient and a matrix. The matrix is composed of at least a nondirect compression filler and a lubricant. The dosage form is adapted to rapidly dissolve in the mouth of a patient and thereby liberate the active ingredient. Preferably, the dosage form has a friability of about 2% or less when tested according to the U.S.P. The dosage form also preferably has a hardness of 15–50 Newtons ("N").

It is desirable that the dosage form dissolve in about 90 seconds or less in the patient's mouth. It is also often desirable that the dosage form include at least one particle. The particle would the active ingredient and a protective material. These particles can include rapid release particles and or sustained release particles.

In a particularly preferred formulation in accordance with the present invention there is provided a hard, compressed, rapidly dissolving tablet adapted for direct oral dosing. The tablet includes particles made of an active ingredient and a protective material. These particles are provided in an amount of between about 0.01 and about 75% by weight based on the weight of the tablet. The tablet also includes a matrix made from a nondirect compression filler, a wicking agent, and a hydrophobic lubricant. The tablet matrix comprises at least about 60% rapidly water-soluble ingredients based on the total weight of the matrix material. The tablet has a hardness of between about 15 and about 50 Newtons, a friability of less than 2% when measured by U.S.P. and is adapted to dissolve spontaneously in the mouth of a patient in less than about 60 seconds and thereby liberate said particles and be capable of being stored in bulk.

The dosage forms described above are able to dissolve rapidly in the mouth of the patient, with a minimum of grit or other organoleptically unpleasant species. Moreover, because the dosage forms are hard and have low friability they can be handled and packaged like other, nonrapidly dissolving dosage forms.

Therefore, in another aspect of the present invention, there is provided a method of making a packaged, orally dissolvable dosage form. The method includes the steps of:

(a) forming a mixture including an active ingredient and a matrix including a nondirect compression filler and a lubricant;

(b) compressing the mixture to form a plurality of hard, compressed, rapidly disintegrable dosage forms including the active ingredient distributed in the orally dissolvable matrix; and (c) storing the dosage forms in bulk prior to packaging. In a preferred embodiment, the dosage forms are then packaged in a lumen of a package such that there is at least one per package. In a preferred particularly preferred embodiment, the dosage forms are then packaged in a lumen of a package such that there more than one per package. Direct compression is the preferred method of forming the dosage forms.

There is also provided hereby an openable and recloseable package containing a plurality of hard, compressed, rapidly dissolving tablets adapted for direct oral dosing as described above.

DETAILED DESCRIPTION OF PREFERRED EMBODIMENT

The present invention is directed to a hard, compressed, rapidly dissolvable dosage form adapted for direct oral dosing. The dosage form includes an active ingredient often in the form of a protected particle, and a matrix. The matrix includes a nondirect compression filler and a lubricant, although, it may include other ingredients as well. The dosage form is adapted to rapidly dissolve in the mouth of a patient. Yet, it has a friability of about 2% or less when tested according to the U.S.P. Generally, the dosage form will also have a hardness of at least about 15–20 Newtons. Not only does the dosage form dissolve quickly, it does so in a way that provides a positive organoleptic sensation to the patient. In particular, the dosage form dissolves with a minimum of unpleasant grit which is tactilely very inconsistent with organoleptic sensation of the dosage form.

"Dosage form," in accordance with the present invention, includes tablets and "slugged cores" used in capsules or caplets (a hybrid tablet/capsule). "Dissolvable," should be understood as describing the action of the dosage form as it is held in the mouth. In this case, the dosage form gets continuously smaller in a process which is conceptually analogous to melting. While the dosage form may also disintegrate into smaller pieces to some extent, particularly where a relatively greater amount of a wicking agent or effervescent disintegrant is used, or where the dosage form is chewed, that is not its principal mechanism. The majority of the matrix material actually dissolves into the saliva while the tablet is in the patients mouth. Ideally, before a patient actually swallows the tablet, substantially all of the rapidly water-soluble components of the matrix have actually dissolved. Moreover, the amount of rapidly water-soluble ingredients in each dosage form is maximized in accordance with the present invention. In this way, as well as in others as described herein, dosage forms in accordance with the present invention are distinguishable from the disintegrable tablets commonly described in the prior art, such as those described in, for example, those of Cousins et al., U.S. Pat. No. 5,464,632. "Rapidly dissolve(able)" means that the rapidly water-soluble ingredients will dissolve sufficiently to allow ingestion as a nongritty solution or slurry in 90 seconds or less, preferably 60 seconds or less and most preferably 45 seconds or less. The rapid dissolution of the dosage form, as well as its composition are designed to minimize the gritty, sandy feel of conventional disintegrable tablets. By minimizing the degree of disintegration during the dissolution of the dosage form, one can avoid adding to the unpleasant organoleptic sensation of grit.

"Water-soluble" in accordance with the present invention has its usual meaning. However, "rapidly water-soluble" means that the ingredient in question will dissolve in a time frame which is consistent with the objects of the invention. For example, a very fine grained or powdered sugar known as a nondirect compression sugar may be used as a filler in the matrix of the present invention. This material, in part because of its chemical composition and in part because of its fine particle size, will dissolve readily in the mouth in a mater of seconds once it is wetted by saliva. Not only does this mean that it can contribute to the speed at which the dosage form will dissolve, it also means that while the patient is holding the dissolving dosage form in his or her mouth, the filler will not contribute a "gritty" or "sandy" texture thus adversely affecting the organoleptic sensation of taking the dosage form. In contrast, direct compression versions of the same sugar are usually granulated and treated to make them larger and better for compaction. While these sugars are water-soluble, they may not be solubilized quickly enough. As a result, they can contribute to the gritty or sandy texture of the dosage form as it dissolves. Dissolution time in the mouth can be measured by observing the dissolution time of the tablet in water at about 37° C. The tablet is immersed in the water without forcible agitation or with minimal agitation. The dissolution time is the time from immersion to substantially complete dissolution of the rapidly water-soluble ingredients of the tablet as determined by visual observation.

To further improve the organoleptic qualities of the dosage forms of the present invention, the amount of nonrapidly dissolvable, i.e., nonrapidly water-soluble materials used is minimized as much as possible. Ideally, the only nonrapidly dissolving species would be the active ingredient, particularly when in protected particle form, and the lubricant. The use of a rapidly water-soluble active ingredient, in a nonprotected form, for example, can further improve the organoleptic properties by further reducing a potential source of grit. A wicking agent may also be used, although, such agents would generally not qualify as rapidly dissolvable under the circumstance. However, if used at all, the amount of wicking agent used in accordance with the present invention is controlled to minimize its impact. Rapidly water-soluble means that the material will be dissolved within about 45 seconds of being wetted with saliva and/or the material must be at least "soluble" pursuant to U.S.P. XXIII, page 10, (1995).

Note that in the context of the present invention, dissolution relates to water-soluble ingredients only. A coated active ingredient is often not water-soluble at all and thus the tablet never completely dissolves. However, because of the high content of rapidly water-soluble ingredients in accordance with the present invention most of that which is water-soluble generally dissolves within the disintegration time of the tablet. Thus, for the same loading of a coated active ingredient, relatively less grit will be present at the time that the tablet has disintegrated.

The active ingredient can include pharmaceutical ingredients, vitamins, minerals and dietary supplements. Pharmaceutical ingredients may include, without limitation, antacids, analgesics, anti-inflammatories, antipyretics antibiotics, antimicrobials, laxatives, anorexics, antihistamines, antiasthmatics, antidiuretics, antiflatuents, antimigraine agents, biologicals, antispaspodics, sedatives, antihyperactives, antihypertensives, tranquilizers, decongestants, beta blockers and combinations thereof. Also encompassed by the terms "active ingredient(s)," "pharmaceutical ingredient(s)" and "active agents" are the drugs and pharmaceutically active ingredients described in Mantelle, U.S. Pat. No. 5,234,957, in columns 18 through 21. That text of Mantelle is hereby incorporated by reference.

As used in this disclosure, the term "vitamin" refers to trace organic substances that are required in the diet. For the purposes of the present invention, the term "vitamin(s)" includes, without limitation, thiamin, riboflavin, nicotinic acid, pantothenic acid, pyridoxine, biotin, folic acid, vitamin $B_{12}$, lipoic acid, ascorbic acid, vitamin A, vitamin D, vitamin E and vitamin K. Also included within the term "vitamin" are the coenzymes thereof. Coenzymes are specific chemical forms of vitamins. Coenzymes include thiamine pyrophosphates (TPP), flavin mononucleotide (FMM), flavin adenine dinucleotive (FAD), Nicotinamide adenine dinucleotide (NAD), Nicotinamide adenine dinucleotide phosphate (NADP), Coenzyme A (CoA), pyridoxal phosphate, biocytin, tetrahydrofolic acid, coenzyme $B_{12}$, lipoyllysine, 11-cis-retinal, and 1,25-dihydroxycholecalciferol. The term "vitamin(s)" also includes choline, carnitine, and alpha, beta, and gamma carotenes.

The term "mineral" refers to inorganic substances, metals, and the like required in the human diet. Thus, the term "mineral" as used herein includes, without limitation, calcium, (calcium carbonate), iron, zinc, selenium, copper, iodine, magnesium, phosphorus, chromium and the like, and mixtures thereof. The term "dietary supplement" as used herein means a substance which has an appreciable nutritional effect when administered in small amounts. Dietary supplements include, without limitation, such ingredients as bee pollen, bran, wheat germ, kelp, cod liver oil, ginseng, and fish oils, amino-acids, proteins and mixtures thereof. As will be appreciated, dietary supplements may incorporate vitamins and minerals.

In general, the amount of active ingredient incorporated in each tablet or dosage form may be selected according to known principles of pharmacy. An effective amount of pharmaceutical ingredient is specifically contemplated. By the term "effective amount," it is understood that, with respect, to for example, pharmaceuticals, a "pharmaceutically effective amount" is contemplated. A "pharmaceutically effective amount" is the amount or quantity of a drug or pharmaceutically active substance which is sufficient to elicit the required or desired therapeutic response, or in other words, the amount which is sufficient to elicit an appreciable biological response when administered to a patient. As used with reference to a vitamin or mineral, the term "effective amount" means an amount at least about 10% of the United States Recommended Daily Allowance ("RDA") of that particular ingredient for a patient. For example, if an intended ingredient is vitamin C, then an effective amount of vitamin C would include an amount of vitamin C sufficient to provide 10% or more of the RDA. Typically, where the tablet includes a mineral or vitamin, it will incorporate higher amounts, preferably about 100% or more of the applicable RDA.

The amount of active ingredient used can vary greatly. Of course, the size of the dosage form, the requirements of other ingredients, and the number of, for example, tablets which constitute a single dose will all impact the upper limit on the amount of pharmacologically active ingredient which can be used. However, generally, the active ingredient is provided in an amount of between greater than zero and about 80% by weight of the finished tablet and, more preferably, in a range of between greater than zero and about 60% by weight thereof. Put in other terms, the active ingredient can be included in an amount of between about 1 microgram to about 2 grams, and more preferably between about 0.01 and about 1000 milligrams per dosage form, i.e., per tablet.

The active ingredient can be provided directly, particularly when it does not have a particularly objectionable taste, i.e., a taste which can not be masked by traditional measures such as the use of sweeteners, flavors and the like. In fact, there may be particular advantages to using bulk active ingredients in this fashion when the active ingredient is rapidly water-soluble. As discussed herein, the higher the level of rapidly water-soluble ingredients, the greater the improvement in the rate of dissolution and the organoleptic feel of the dosage form in the mouth of the patient.

However, the active ingredient is preferably in a particle, granular, microgranular or crystalline form protected by a protective material. This protective material can be an adsorbate, a microgranule such as disclosed in Sparks et al., U.S. Pat. No. 4,940,588, or a coating which forms microcapsules and/or microparticles as described in, without limitation, Wehling et al., U.S. Pat. No. 5,178,878. Combinations of these are also contemplated, i.e., a coated adsorbate. In addition, protection can be provided by agglomeration or the formation of a matrix as is conventional. The dosage forms of the present invention may also include a plurality of different active agents each protected by a different means.

The protective materials used in accordance with the present invention may include any of the polymers conventionally utilized in the formation of microparticles, matrix-type microparticles and microcapsules. Among these are cellulosic materials such as naturally occurring cellulose and synthetic cellulose derivatives; acrylic polymers and vinyl polymers. Other simple polymers include proteinaceous materials such as gelatin, polypeptides and natural and synthetic shellacs and waxes. Protective polymers may also include ethylcellulose, methylcellulose, carboxymethyl cellulose and acrylic resin material sold under the registered trademark EUDRAGIT by Rhone Pharma GmbH of Weiterstadt, Germany.

Generally, when a coating is used, it is preferred that the coating be used in at least about 5 percent based on the weight of the resulting particles. More preferable, the coating should constitute at least about 10 percent by weight of the particle. The upper limit of protective coating material used is generally less critical, except that where a rapid release of the active ingredient is desired, the amount of coating material should not be so great that the coating material impedes the release profile of the active agent or pharmaceutical ingredient when ingested. Thus, it may be possible to use greater than 100 percent of the weight of the core, thereby providing a relatively thick coating. Generally, however, no more than about 96 percent of the weight of the particle (drug an coating) will be coating material and, more preferably, no more than about 75 percent of the weight of the particulate will be coating. Described another way, the protective material is generally provided in an amount of between about 5 and about 96% by weight of the protected particle. More preferably, the amount is provided in a range of between about 5 and about 75% by weight based on the weight of the active protected ingredient. Of course, the use of coatings to provide for a sustained or controlled release may change these requirements. See Barry et al., U.S. Pat. No. 5,055,306, the text of which is hereby incorporated by reference and a copy is attached.

Particles formed from the active ingredients in accordance with the present invention may range in size from a few microns to as much as 1,500 microns. The lower limit of the size is not important, provided integrity is not compromised. Particles should generally not be larger than 1,200 microns and preferably be no larger than 850 microns. Of course, the larger the particles, the greater the impact on the organoleptic feel of the formulation once the dosage form dissolves.

Particles in accordance with the present invention generally relate to discrete particles containing an active ingredient and a coating protective material, if any. Particles may be a discrete granular material which has been independently and substantially (greater than about 90% of the particles completely coated) coated with a coating material.

Of course, when coated particles are produced, it is preferred that each individual unit of active ingredient, whether in the form of a liquid, a granule, or a powder, be substantially completely coated. In the case of, for example, extended release or sustained release microparticles, (also referred to as controlled release, delayed release or modified release), providing such complete coating helps ensure the desired level and type of release. When using an encapsulant or a coating to assist in taste-masking, complete coating helps ensure that the tastebuds of a patient are not exposed to the objectionable-tasting material. The more successful and complete the coating the better, in terms of its intended properties. When, for example, rapid-release enteric coatings are used, substantially complete coating or encapsulation helps ensure that the active ingredient is not exposed to moisture or acid in the stomach. Thereafter, once the encapsulated drug reaches the intestines, the coating can, for example, disintegrate or rapidly dissolve such that it provides minimal interference with the normal dissolution profile of the drug when compared to the uncoated drug. In this aspect of the present invention, however, the term particle also includes a crystalline or granular base material which has been imperfectly coated such that some or all of the particles are not completely coated with the protective material. Also useful in accordance with the present invention and falling within the scope of the term particle, are agglomerate matrices whereby an agglomerate is dispersed in a wet coating material which is later broken up, ground or milled. The result may be incompletely coated particles or particles which are stuck together with the coating material serving as the glue.

For example, under certain circumstances, the use of an agglomerate matrix will provide adequate taste-masking and/or adequate protection of the active ingredient. Alternatively, the use of a matrix and/or agglomerates may sufficiently slow the rate of release of the active ingredient so as to allow it to be a sustained release formulation. In addition to the coating materials just described, various other additives, such as, for example, cross linkers, pore-formers, swelling agents, solubility modifiers, glidants, plasticizers and the like, may be included within the coating or protective material.

Ingredients and methods for making particles, including microcapsules, coated granules, agglomerates, etc., are well-known in the art and all such methods are contemplated. Methods of microencapsulation, for example, are described in the aforementioned Lieberman text, *Pharmaceutical Dosage Form: Tablets Volume* 1, Second Edition, New York, 1989, at pages 372–376. The disclosure of Lieberman is hereby incorporated by reference herein. One method taught in Lieberman is the technique of phase separation or coacervation which involves processing three mutually immiscible phases, one containing the pharmaceutical ingredient, another containing the protective coating material and a third containing a liquid vehicle used only in the manufacturing phase. The three phases are mixed and the protective material phase deposits by absorption on the pharmaceutical ingredient phase. After this step, the protective material phase is converted to a substantially solid form by cross-linking or by removal of solvent from this phase.

Other common techniques may be used for forming matrix-type particles wherein the pharmaceutical ingredient is dispersed in the protective material. For example, the pharmaceutical ingredient and a solution of a polymeric protective material may be sprayed to form droplets and contacted with a gas such as hot air so as to remove the solvent from the droplets. Such a mixture may also be dried to a solid and then comminuted to form the particles. Alternatively, the mixture of the pharmaceutical ingredient and polymeric solution may be mixed with an immiscible liquid phase and the solvent may be removed through this phase. The mixing step may include emulsification of the phase bearing the pharmaceutical ingredient and the protective material in the immiscible liquid phase. Preferably, a spray coating or coacervation coating technically may be used.

Sustained release in accordance with the present invention means that the active ingredient is released into the bloodstream in a manner which is intentionally slower than the bioavailability of the same drug if administered in a non-sustained released form such as in bulk. Generally, a drug will exhibit at least a 25% decrease in its rate of absorption bioavailability relative to the uncoated drug. Most preferably, sustained release formulations are formulations which administer the active ingredient over a period of ten hours or greater and most preferably, between about 12 and about 24 hours. All such release rate control in the formulations of the present invention must come from the particles themselves as, ideally, the remainder of the dosage form has dissolved.

In contrast, rapid release dosage forms in accordance with the present invention are those in which the drug is rapidly released from the encapsulant, coating, or other protective material when desired. To the extent possible, the effect of the protective material under such circumstances will be minimal in terms of reducing the normal bioavailability of the same drug if unprotected. Thus, for example, where a coating is used to taste mask the objectionable flavor of a material, it is important that that coating be intact, to the extent necessary to serve its taste-masking function, while the dosage form is in the mouth of the patient. However, once the patient has swallowed there is no longer a need to protect the tastebuds from the drug. It may be desirable that the drug be immediately bioavailable. In such a circumstance, it is desirable for the coating to either rupture in order to release its contents, dissolve thereby exposing its contents or allow the gastric juices in the stomach to permeate through and dissolve the active ingredient such that the bioavailability of the coated drug remains, as nearly as possible, the same as that of the same drug if administered in an unprotected form. Thus, if a tablet including nonprotected active ingredients would need normally to be dosed every four or every six hours, then the rapid release dosage form in accordance with the present invention would also have to be administered on that same basis. A rapid release dosage form in accordance with the present invention is one which disintegrates rapidly in the mouth to form a suspension of particles which, once they clear the mouth, will release their contents so as not to interfere with the normal bioavailability of the active ingredient.

Generally, the particles in accordance with the present invention are provided in an amount of between greater than zero to about 75% by weight based on the weight of the finished dosage form. More preferably, the particles are provided in an amount of between greater than zero and about 60% by weight.

In attempting to balance the various competing objectives of the dosage forms of the present invention, namely; compressibility at conventional pressures, hardnesses and friability (which allow for certain processing and packaging advantages) and rapid dissolution in the mouth, several traditionally held values within the pharmaceutical industry had to be transgressed. This is most apparent from the composition of the matrix and its effects on these dosage forms. The matrix includes at least two ingredients: a nondirect compression filler and a lubricant. The use of both ingredients, particularly in the amounts contemplated, really sets the present invention apart. The matrix will assist in preventing the rupture of any microcapsules, microparticles or other protected active ingredient incorporated therein during compression. The matrix will also assist in the rapid dissolution of the dosage form in the mouth. Finally, the matrix provides a positive organoleptic experience to the patient.

The type of filler used provides one example of the uniqueness of the matrix and the dosage forms of the invention. As illustrated by Cousins et al., it is traditional to use a direct compression sugar or other highly compressible fillers when attempting to produce tablets of a certain hardness and/or friability. However, it was determined that the particle sizes of such sugars had a dramatic affect on the manner in which the resulting tablets behave and feel in the mouth. While such sugars will eventually dissolve, because of their particle size and the processing that was done to improve their compressibility and fluidity, significant time is necessary before dissolution is complete. Thus, while the use of such sugars may allow for the tablet to disintegrate within the mouth, the result is relatively slow and a relatively high proportion of grit is generated. (Grit in the Cousins et al. formulation are attributable to the coated active ingredient, the relatively high proportion of non-water-soluble excipients such as disintegrants, as well as the relatively large grained direct compression sugars used.)

Of course, one might expect to be able to overcome this particular problem by changing the particle size of the direct compression sugar, such that it will dissolve more quickly. However, as is well known in the pharmaceutical industry, decreasing the particle size of the sugar decreases its compressibility and fluidity. This was thought to undermine the ability to produce uniformly hard, and nonfriable tablets. While such smaller particles might dissolve rapidly within the mouth, they were thought to be difficult, if not impossible, to compress, particularly at production speeds; thus, the need for specialized direct compression versions of these same sugars.

Therefore, it was surprising to discover that nondirect compression fillers may in fact be used in the production of a hard, nonfriable, directly compressible, yet rapidly dissolvable, in-mouth dosage form, particularly in an automated, commercial production setting.

Any conventional material can be used as a filler in accordance with the present invention, so long as it meets the overall objectives hereof. The filler must be rapidly dissolvable when a tablet produced from same is placed in the mouth. This means that the material must be significantly rapidly water-soluble. In addition, generally, the particle size of the filler will be relatively small, particularly compared to direct compression fillers.

Generally, direct compression excipients, particularly fillers and binders, are specialty excipients. In most cases, they are common materials that have been physically modified to impart greater fluidity and compressibility. In the case of sugars, such as, for example, dextrose, this generally means granulation to increase particle size. Direct compression mannitol, for example, generally has a minimum of at least about 80% average particle size over 100 microns. Other commercially available direct compression mannitols have a minimum particle size standard of greater than 90% over 200 microns. The opposite is true of the fillers in accordance with the present invention. While direct compression fillers may have at least 85% of the particles over 100 microns in size, often 85% of the particles of filler used in the present invention are significantly under 100 microns. In accordance with the present invention, average particle size generally ranges from between about 10 and about 80 microns, and most preferably, between about 20 to about 65 microns.

Particularly preferred fillers, in accordance with the present invention are nondirect compression sugars and sugar alcohols which meet the specifications discussed above. Such sugars and sugar alcohols include, without limitation, dextrose, mannitol, sorbitol, lactose and sucrose. Of course, dextrose, for example, can exist as either a direct compression sugar, i.e., a sugar which has been modified to increase its compressibility, or a nondirect compression sugar.

Generally, the balance of the formulation can be matrix. Thus the percentage of filler can approach 100%. However, generally, the amount of nondirect compression filler useful in accordance with the present invention ranges from about 25 to about 95%, preferably between about 50 and about 95% and more preferably from about 60 to about 95%. In contrast, the prior art, as represented by Cousins et al. uses only up to about 42% of a filler and it is a direct compression sugar as well.

It has also been surprisingly found that when formulating dosage forms in accordance with the present invention, a relatively high proportion of lubricant should be used when compared to the prior art. Lubricants, and in particular, hydrophobic lubricants such as magnesium stearate, are generally used in an amount of between about 0.25 to about 5%, according to the Handbook of Pharmaceutical Excipients. However, as Cousins et al. amply demonstrate, when making a rapidly disintegrable tablet for direct in-mouth administration, one would seek to minimize the amount of magnesium stearate or other lubricant used. These hydrophobic lubricants generally interfere with disintegration and dissolution. They can also interfere with the compressibility of the material hindering the ability to make hard, nonfriable tablets and the like. Not surprisingly, Cousins et al., who were seeking to make hard tablets that will rapidly disintegrate, teach the use of an amount of magnesium stearate which ranges from between about 0.4 to about 0.5% by weight, i.e., at the lower portion of the conventional range.

Moreover, the generally high level of nondirect compressible filler and the relatively low proportions of disintegrants used (if at all) in accordance with the present invention, would also lead one to expect to minimize the amount of lubricant used. However, it has been found that the amount of lubricant used can be double, triple or even quadruple that proposed in Cousins et al. Specifically, the amount of lubricant used can generally range from between about 1 to about 2.5% by weight, and more preferably between about 1.5 to about 2% by weight. Yet, despite the use of this relatively high rate of lubricant, the formulations in accordance with the present invention still exhibit a superior compressibility, hardness, and rapid dissolution within the mouth.

Hydrophobic lubricants useful in accordance with the present invention include alkaline stearates, stearic acid, mineral and vegetable oils, glyceryl behenate and sodium stearyl fumarate. Hydrophilic lubricants can also be used.

The dosage forms in accordance with the present invention preferably have a hardness of at least about 15 Newtons and are designed to dissolve spontaneously and rapidly in the mouth of a patient in less than about 90 seconds to thereby liberate the particles. Preferably the dosage form will dissolve in less than 60 seconds and even more preferably 45 seconds. This measure of hardness is based on the use of small tablets of less than about 0.25 inches in diameter. A hardness of at least about 20 Newtons is preferred for larger tablets. Most preferably, however, the dosage forms in accordance with the present invention have a hardness of between about 20 and about 50 Newtons and, more preferably, between about 25 and about 45 Newtons. Most preferably, the tablet will have a hardness of about 35 Newtons. Proportionate hardnesses are expected for tablets of different sizes.

It is quite surprising, however, that while relatively hard tablets can be produced in accordance with the present invention (hardnesses of 15–20 Newtons through about 50 Newtons) and despite the absence of traditionally directly-compressible fillers, relatively modest compressive force is required to produce substantially hard tablets in accordance with the present invention. Cousins et al. teach compaction forces of between 16 and 21 kN. Moreover, the minimum compressive force required for pure tablets of granular mannitol, i.e., a direct compression sugar, is at least 7.35 kN. However, in accordance with the present invention, rapidly dissolving tablets can be produced using compaction forces ranging from between about 3 to about 13 kN. This has significant advantages in terms of maintaining the structural integrity of any protective layer which may coat the active ingredient. In addition, it reduces the stress and wear on tablet-press equipment.

Unexpectedly, the dosage forms in accordance with the present invention will have a friability, as measured by U.S. Pharmacopoeia 23, 1995, Chap. 1216 entitled "Tablet Friability," of less than about 2% and, more preferably, less than about 1%. Thus, it is possible in accordance with the present invention to produce in-mouth, rapidly disintegrable dosage forms, including those having effervescent couples, which have friabilities comparable to those of conventional tablets. This allows the dosage forms of the present invention to be produced using traditional high-speed tablet presses. In addition, the resulting tablets can be stored in bulk and transported to packaging devices using traditional high-speed conveyors and/or, for example, vibrational conveyors.

Another aspect of the present invention is a method of making a packaged, orally disintegrable tablet or other dosage form. The method includes the steps of forming a mixture of the active ingredient and the matrix; and compressing the mixture to form a plurality of hard, compressed, rapidly disintegrable tablets adapted for direct oral dosing. Preferably, tablets are formed by "direct compression." "Direct compression" as used herein means that one can avoid the difficulty and expense of a wet or dry granulation prior to compression. The tablets will preferably have a hardness of at least about 15 Newtons and will be adapted to dissolve in the mouth of a patient within about 90 seconds to liberate the particles. In most formulations, the hardness may be at least 20 Newtons and the tablet dissolves in 45 seconds or less. Other conventional tableting or slugging methods known in the art are also contemplated. Indeed, any method in which a mixture of the active ingredient, often in the form of a protected particle, and the matrix are compressed into a solid dosage form having the properties disclosed herein are acceptable. After tableting or slugging, the dosage forms can be packaged in the lumen of a package or stored in bulk.

One of the principle advantages of the orally dissolvable tablets of the present invention is that they can be manufactured and stored in drums, bulk bins or hoppers, after tablet compression as is typical for tablets in the pharmaceutical industry. This is a property which is not found in most rapidly orally disintegrable tablets because of their friability. In turn, this attribute provides several significant advantages. First, with most friable, orally disintegrable tablets, the rate limiting step in production is the speed at which the tablets can be individually handled and placed in a protective, usually specially designed, blister-style package. The tablets are too fragile to withstand the forces involved in being dumped into the bulk-hopper of a packager or into some other form of intermediate or long-term storage vessel. Thus, the speed of production of the tablets is limited by the rate of packaging.

In accordance with the present invention, however, because of the relatively low friability and the hardness of the resulting orally dissolvable tablets, they can be dumped into a hopper in bulk or can be stored in drums or other containers. This allows the manufacturer to complete production of the tablets at maximum tableting speed. Tablet presses can then be dedicated to other products while the orally disintegrable tablets of the present invention are packaged as is convenient.

Storing in bulk, in accordance with the invention, does not mean that tablets need to be stored for a long time. The residence time of tablets as they are dumped, in bulk, into the feed hopper of a high speed packager is contemplated.

The present invention allows for quality control of the tablets before they are packaged. This is of tremendous significance to the cost of production. Standard quality control procedures on orally disintegrable tablets involves testing the tablets that result from the line, i.e., tablets that have already been packaged. If a batch or lot of tablets has to be failed, the materials and the packaging may be lost. In some instances, the cost of the packaging is significantly higher that the cost of the drug material itself. By unshackling the tablet production and tablet packaging operations, one can test the tablets before package and therefore, eliminate the added expense of throwing away perfectly good packaging.

In addition, because of the relatively low friability and hardness of the orally dissolvable tablets in accordance with the present invention, it is possible to provide tablets in less costly and more cost-effective packaging. Currently, fragile, orally disintegrable dosage forms must be individually packaged in a very protective and very expensive blister pack. However, the tablets of the present invention can be placed in conventional openable and recloseable multi-tablet bottles or other similar packaging. That is to say that in accordance with the present invention, it is possible to provide more than a single dose in the lumen of a single, reopenable and reclosable package. Not only are such packages considerably less expensive over the cost of the number of tablets provided, but they are also far more efficient in terms of processing. In addition, two-sided foil and other relatively soft, pliant envelope-type packages may be used in combination with the tablets in accordance with the present invention. It is not possible to use such packages, or even less protective blister-packs, with the relatively friable orally-disintegrable tablets of the prior art.

In addition, in accordance with the present invention, conventional tablets feeders can be used to feed the tablets into any type of packaging equipment. Not only can the friable tablets of the prior art not withstand traditional hoppering or storage, they also cannot withstand the forces involved in traditional feeding systems. Such systems normally consist of mechanisms which take bulk random tablets, capture them, align them, and place them into a package.

This provides a tremendous advantage in terms of the processability of tablets of the present invention and also provides tremendous advantages in terms of capital expenditures. By the use of the present invention, one can produce tablets which can be processed through totally conventional tableting methodologies and using conventional tableting equipment. This saves thousands to hundreds of thousands of dollars by removing the need for specialized packaging and handling equipment. It also increases the through-put of the tablets in question.

Another surprising aspect of the present invention is its workability. Cousins et al. uses a direct compression sugar and takes a mixture of all of its excipients and prepares them by dry or wet granulation prior to mixing with the active ingredient. This is a conventional method of improving the compressibility of materials and is often used even when direct compression excipients are employed.

However, the formulations of the present invention, despite their use of relatively high amounts of generally nondirectly compressible fillers, can be formulated using direct compression. Direct compression involves mixing the various ingredients in a mixing vessel and then metering them directly into a tablet press whereupon they are pressed into tablets.

It is also surprising that, in accordance with the present invention, rapidly dissolving tablets can be manufactured with not only high levels of lubricant, but also that lubricant blend times of 10 to 25 minutes and greater can be used. However, according to the present invention, blend times of ten minutes and greater can be used without compromising compressibility, disintegration and dissolution of the tablets. In fact, this even improves the flow characteristics of this material.

In summary, it has been found that nondirect compression fillers, namely powdered mannitol, can be directly compressed, using lower than expected compression forces, at fairly high levels of lubricant and long lubricant blending. The result is a hard, yet rapidly orally dissolvable tablet.

In accordance with the present invention, the dosage forms can have any size conventional in the industry. However, dosage forms of up to about 2.54 centimeters or 1 inch, are generally preferable. It is also preferred that tablets produced have generally convex surfaces. Applicants have found that, by insuring that the tablet in question has as few sharp edges as possible, it is also possible to help retard the dusting or break-up of the tablets in accordance with the present invention, particularly during handling and shipping. Other shapes which retard the formation of sharp edges are also specifically contemplated hereby.

In addition to the ingredients previously discussed, the matrix may also include wicking agents, noneffervescent disintegrants and effervescent disintegrants. Wicking agents are compositions which are capable of drawing water up into the dosage form. They help transport moisture into the interior of the dosage form. In that way the dosage form can dissolve from the inside, as well as from the outside.

Any chemical which can function to transport moisture as discussed above can be considered a wicking agent. Wicking agents include a number of traditional noneffervescent disintegration agents. These include, for example, microcrystalline cellulose (AVICEL PH 200, AVICEL PH 101), Ac-Di-Sol (Croscarmelose Sodium) and PVP-XL (a crosslinked polyvinylpyrrolidone); starches and modified starches, polymers, and gum such as arabic and xanthan. Hydroxyalkyl cellulose such as hydroxymethylcellulose, hydroxypropylcellulose and hydroxyopropylmethylcellulose, as well as compounds such as carbopol may be used as well.

The conventional range of noneffervescent disintegrant agents used in conventional tablets can be as high as 20%. However, generally, the amount of disintegration agent used ranges from between about 2 and about 5%, according to the Handbook of Pharmaceutical Excipients. Understandably, however, when a rapidly disintegrating dosage form is envisioned, the relative proportion of disintegration agent used will be increased. Cousins et al., for example, requires from about 6.1 to about 13.3% reticulated PVP, as described in its various examples.

In accordance with the preferred embodiments of the present invention, the amount of wicking agents used ranges from between 2 to about 12% and preferably from between 2 to about 5%. This is surprising as tablets containing the same amount of the same materials used as disintegration agents normally exhibit disintegration times on the order of tens of minutes. In accordance with the preferred embodiments of the present invention, dissolution occurs in under 90 seconds and most preferably under 45 seconds. This also underscores the fact that while there may be some incidental disintegration due to the inclusion of these elements, their principle effect in the formulations of the present invention is that of a wicking agent.

It is also possible, of course, to include noneffervescent disintegrants which may not act to wick moisture, if desirable. In either event, it is preferable to use either rapidly water-soluble, noneffervescent disintegrants or wicking agents and/or to minimize the use of generally non-water-soluble wicking agents or noneffervescent disintegrants. Nonrapidly dissolvable, nonrapidly water-soluble elements if used in sufficient quantity, can adversely affect the organoleptic properties of the tablets as they dissolve within the mouth and therefore should be minimized. Of course, wicking agents or noneffervescent disintegrants which are rapidly water-soluble as discussed herein can be used in greater quantity and they will not add to the grittiness of the formulation during dissolution. Preferred wicking agents in accordance with the present invention include crosslinked PVP, although, the amounts of these must be controlled as they are not rapidly water-soluble.

In addition, it may be desirable to use an effervescent couple, in combination with the other recited ingredients to improve the disintegration profile, the organoleptic properties of the material and the like. Preferably, the effervescent couple is provided in an amount of between about 0.5 and about 50%, and more preferably, between about 3 and about 15% by weight, based on the weight of the finished tablet. It is particularly preferred that sufficient effervescent material be provided such that the evolved gas is less than about 30 $cm^3$, upon exposure to an aqueous environment.

The term "effervescent couple" includes compounds which evolve gas. The preferred effervescent couple evolve gas by means of a chemical reaction which takes place upon exposure of the effervescent disintegration couple to water and/or to saliva in the mouth. This reaction is most often the result of the reaction of a soluble acid source and an alkali monohydrogencarbonate or other carbonate source. The reaction of these two general compounds produces carbon dioxide gas upon contact with water or saliva. Such water-activated materials must be kept in a generally anhydrous state and with little or no absorbed moisture or in a stable hydrated form, since exposure to water will prematurely disintegrate the tablet. The acid sources may be any which are safe for human consumption and may generally include food acids, acid and hydrite antacids such as, for example: citric, tartaric, malic, fumaric, adipic, and succinics. Carbonate sources include dry solid carbonate and bicarbonate salt such as, preferably, sodium bicarbonate, sodium carbonate, potassium bicarbonate and potassium carbonate, magnesium carbonate and the like. Reactants which evolve oxygen or other gasses and which are safe for human consumption are also included.

In the case of the orally dissolvable tablets in accordance with the present invention, it is preferred that both the amount and the type of disintegration agent, either effervescent or noneffervescent, or the combination thereof be provided sufficient in a controlled amount such that the tablet provides a pleasant organoleptic sensation in the mouth of the patient. In some instances, the patient should be able to perceive a distinct sensation of fizzing or bubbling as the tablet disintegrates in the mouth. In general, the total amount of wicking agents, noneffervescent disintegrants and effervescent disintegrants should range from 0–50%. However, it should be emphasized that the formulations of the present invention will dissolve rapidly and therefore, the need for disintegrating agents is minimal. As illustrated in the examples, appropriate hardness, friability and dissolution times can be obtained even without effervescent disintegrants or high quantities of wicking agents.

The use of a nondirect compression filler eliminates the need for many conventional processing steps such as granulation and/or the need to purchase more expensive pre-granulated, compressible fillers. At the same time, the resulting dosage form is a balance of performance and stability. It is robust enough to be conventionally produced using direct compression. It is robust enough to be stored or packaged in bulk. Yet, it rapidly dissolves in the mouth while minimizing the unpleasant feel of conventional disintegrating tablets to the extent possible.

This last point bears further emphasis, by the use of nondirect compression fillers, by maximizing the quantity of rapidly dissolving, rapidly water-soluble ingredients and by the use of a relatively high lubricant content, dosage forms can be produced which can dissolve rapidly yet are robust as described herein. The difference between dissolution and disintegration is not a trivial one. Conventional disintegrating tablets may disintegrate in 45 seconds or less. However, because of the relatively high content of non-water-soluble and nonrapidly water-soluble components, what remains is material which cannot dissolve or has not dissolved. In contrast, and in accordance with the present invention, all of the rapidly water-soluble materials have dissolved leaving a relatively small percentage of nondissolved and/or dissolvable material.

The following patents are hereby incorporated by: Cousins et al., U.S. Pat. No. 5,464,632; Chavkin, U.S. Pat. No. 4,613,497; Howell, U.S. Pat. No. 3,962,417; Cooper, GB 3,160; Sparks et al., U.S. Pat. No. 4,940,588; Wehling et al., U.S. Pat. No. 5,178,878; Bolt et al., U.S. Pat. No. 5,225,197; and Barry et al., U.S. Pat. No. 5,055,306. These patents describe various active ingredients, excipients and general methods of making particles and dosage forms and they are included for that reason.

EXAMPLES

Example 1

80 mg APAP (acetaminophen), using Nu-Tab Compressible Sugar (sucrose) as filler:

| Formula: | | |
|---|---|---|
| Coated APAP (20% coating) | 15.4% | |
| Compressible Sugar | 64.3% | |
| Effervescence | 4% | |
| Sweetener | 4.6% | |
| Glidant | 0.3% | |
| Lubricant | 1.5% | |
| Wicking Agent | 5% | |
| Flavor | 3.8% | |
| Color | 0.3% | |
| Total | 650 | mg total tablet weight |

Tablets were produced using a direct compression method as follows: All of the material, except the lubricant were weighed and blended for a period of between about 30 and about 50 minutes. Thereafter, the lubricant was added and the mixture was blended for an additional 5 to 15 minutes. The blend was then tableted on a conventional 6 or 16 stage rotating tablet press at 25–30 revolutions per minute. Tablets were compressed using an average compression force of 10.36 kN—the average ejection force was 184.6 N. The average in-vitro disintegration time was 727.8 seconds and friability was 0.87%. The result was a slowly disintegrating tablet and an unpleasant, gritty organoleptic experience for the patients.

The following procedure was followed to determine in-vitro disintegration of tablets. A constant temperature water bath was turned on and allowed to equilibrate to 37° C. 150 mL of DI water was placed in 8 oz. clear plastic cups, which in turn were placed in the constant temperature water bath. The water in the cups was allowed to equilibrate to 37° C., checking with a thermometer. Then, one tablet was placed in a cup and a stopwatch was started simultaneously. Disintegration was complete when the tablet had broken apart and only water-insoluble or nonrapidly water-soluble particles remained. When the tablet had reached the endpoint, the timer was stopped. Average and % RSD were calculated. In-vivo disintegration of Hard Tablets was measured as follows: Tablets were placed in the mouth and are sucked or moved around with the tongue. (Tablets are not chewed.) The tablet disintegration endpoint occurs when the body of the tablet has disintegrated into particles. The degree of dissolution at that point involved a consideration of the organoleptic properties of the amount of remaining particles.

Example 2

80 mg APAP using FINLAC DC (direct compression Lactitol) as filler:

| Formula: | | |
|---|---|---|
| Coated APAP | 15.4% | |
| FINLAC DC | 64.3% | |
| Effervescence | 4% | |
| Sweetener | 4.6% | |
| Glidant | 0.3% | |
| Lubricant | 1.5% | |
| Wicking Agent | 5% | |
| Flavor | 3.8% | |
| Color | 0.3% | |
| Total | 650 | mg total tablet weight |

These tablets were produced as described in Example 1 and were compressed using an average compression force of 7.68 kN—the average ejection force was 162.1 N. The average in-vitro disintegration time was 100.2 seconds and friability was 0.99%. The result was a slowly disintegrating tablet and an unpleasant, gritty organoleptic experience for the patients.

Example 3

80 mg APAP using Sorbitol Instant Pharma (direct compression sorbitol) as filler:

| Formula: | Coated APAP | 15.4% | |
|---|---|---|---|
| | Sorbitol Instant Pharma | 64.3% | |
| | Effervescence | 4% | |
| | Sweetener | 4.6% | |
| | Glidant | 0.3% | |
| | Lubricant | 1.5% | |
| | Wicking Agent | 5% | |
| | Flavor | 3.8% | |
| | Color | 0.3% | |
| | Total | 650 | mg total tablet weight |

These tablets were produced as described in Example 1 and were compressed using an average compression force of 5.65 kN—the average ejection force was 122.3 N. The average in-vitro disintegration time was 227.2 seconds and friability was 1.14%. The result was a slowly disintegrating tablet and an unpleasant, gritty organoleptic experience for the patients.

Example 4

| Coated Paracetamol Powder (78.2%) | 15.7% |
|---|---|
| Powdered Mannitol (non-direct compression sugar), USP | 64.0% |
| Sodium Bicarbonate, No. 1 USP | 2.3% |
| Citric Acid, Anhydrous Fine Granular USP | 1.7% |
| Artificial sweetener, Dried | 4.6% |
| Wicking Agent | 5.8% |
| Glidant | 0.3% |
| Magnesium Stearate, NF | 1.5% |
| Artificial Flavor | 3.8% |
| Artificial Color | 0.3% |
| | 650.0 mg Total tablet weight |

Two different batches of these tablets were produced. In the first batch, tablets were produced as described in Example 1. The resulting tablets had a hardness of 35 Newtons and a friability of 1.8%. The average in-vitro disintegration time was 36 seconds. The second batch was produced as described in Example 1. The average in-vitro disintegration time was 44 seconds and the tablets had a hardness of 50 Newtons and a friability of 0.5%. The result was a fast dissolving tablet with a minimum of grit and a pleasant organoleptic experience.

Example 5

Pseudoephedrne HCl/Chlorphenirmine Maleate; 7/16"

| Formula: | Coated Pseudoephedrine HCL (40% coated) | 5% | |
|---|---|---|---|
| | Coated Chlorpheniramine Maleate (90% coated) | 2% | |
| | Powdered Mannitol | 71.9% | |
| | Effervescence | 4% | |
| | Sweetener | 4.8% | |
| | Glidant | 0.3% | |
| | Microcrystalline Cellulose | 2% | |
| | Lubricant | 1.5% | |
| | Wicking Agent | 5.8% | |
| | Flavor | 2.4% | |
| | Color | 0.3% | |
| | Total | 500 | mg total tablet weight |

These tablets were produced as described in Example 1 and compressed with an average force of 9.38 kN (38N hardness), and average ejection force of 212.2N. The tablets disintegrated in 22.83 seconds in vitro and 20–30 seconds in vivo. At that time, most, if not all of the rapidly water-soluble ingredients (>about 75%) had dissolved. Friability was 1.37%.

Example 6

Cimetidine Tablets, ½"

| Formula: | Coated Cimetidine (32% coated) | 22.5% | |
|---|---|---|---|
| | Powdered Mannitol | 60.2% | |
| | Effervescence | 4% | |
| | Sweetener | 5% | |
| | Wicking Agent | 6% | |
| | Glidant | 0.3% | |
| | Lubricant | 1.5% | |
| | Flavor | 0.5% | |
| | Total | 650 | mg total tablet weight |

These tablets were produced as described in Example 1 and were compressed with an average force of 8.52 kN (43N) hardness, and an average ejection force of 215.6N. The tablets disintegrated in 26.31 seconds in vitro and 20–30 seconds in vivo. Friability was 1.12%.

Example 7

Acetaminophen, 9/16"

| Formula: | Coated APAP (20% coating level) | 31.3% |
|---|---|---|

-continued

| | | |
|---|---|---|
| Powdered Mannitol | 49.6% | |
| Effervescence | 4% | |
| Sweetener | 5% | |
| Microcrystalline Cellulose | 2% | |
| Glidant | 0.3% | |
| Lubricant | 1.5% | |
| Wicking Agent | 5.8% | |
| Flavor | 0.5% | |
| Total | 1,000 | mg total tablet weight |

These tablets were produced as described in Example 1 and were compressed with an average force of 12.13 kN (approx. 83N hardness), and had an average ejection force of 286.4N. The tablets disintegrated in 23.42 seconds in vitro and 30–40 seconds in vivo. Friability was 0.82%.

Example 8

80 mg APAP, ½"

| Formula: | | | |
|---|---|---|---|
| | Coated APAP (20% coated) | 15.4% | |
| | Powdered Mannitol | 66.6% | |
| | Citric Acid | 1.7% | |
| | Sweetener | 4.6% | |
| | Glidant | 0.3% | |
| | Lubricant | 1.5% | |
| | Wicking Agent | 5.8% | |
| | Flavor | 3.8% | |
| | Color | 0.3% | |
| | Total | 650 | mg total tablet weight |

These tablets produced as described in Example 1 and were compressed with an average force of 10.27 kN (40N hardness) and had an average ejection force of 223.87N. The tablets disintegrated in 20.42 seconds in vitro and in 20–30 seconds in vivo. The friability was 1.0%. It should be noted that the above formulation, while having a hardness of 40 Newtons and a friability of 1%. Disintegration and indeed, dissolution occurred in between 20 and 30 seconds, without the use of an effervescent disintegrant.

Example 9

APAP coated with 10% Eudragit—⅝" hard tablet—target hardness is 95N+/−10N.

| Formula: | | | |
|---|---|---|---|
| | Coated Acetaminophen (10% coating factor) | 944 | mg |
| | Aspartame | 50 | mg |
| | Disintegrant | 89 | mg |
| | Lubricant | 5 | mg |
| | Flavor | 12 | mg |
| | Total | 1100 | mg total tablet weight |

Tablets were compressed using an average compression force of 23.28 kN (109N Hardness) and had an average ejection force of 802.8N. Disintegration time in vitro was 43.90 seconds in vivo was greater than 40 seconds. Friability was not measured. Tablets tasted terrible and were extremely gritty.

| Example 10. | | | |
|---|---|---|---|
| | Coated APAP (7% coated with ethylcellulose) | 530 | mg |
| | Compressible Sugar | 160 | mg |
| | Microcrystalline Cellulose | 90 | mg |
| | Crospovidone | 60 | mg |
| | Sodic Carbocymethylcellulose | 50 | mg |
| | Silicon Dioxide | 6 | mg |
| | Lubricant | 4 | mg |
| | Sweetener | 25 | mg |
| | Flavor | 15 | mg |
| | Magnesium Trisilicate | 50 | mg |
| | Total | 990 | mg total tablet weight |

Tablets were compressed using an average compression force of 35.68 kN (101N Hardness) and had an average ejection force of 362.8N. Disintegration time in vitro was 65.59 seconds.

Examples 9 and 10 are very similar to the formulations described in the Cousins et al. patent discussed herein. These examples illustrate many of the advantages of the present invention. First, it should be noted that in both cases, the relative proportion of rapidly water-soluble materials was minimal. Thus, when these tablets disintegrate, the patient is left with a mouth full of particulate materials which must be swallowed, rather than a slurry or solution as would result from the present invention. At very least, the present invention would minimize the level of particulate and grit. Second, while the formulations of examples 9 and 10 could disintegrate in about 45 and about 65 seconds respectively, the formulations of the present invention as illustrated in the examples 4–8 were able to dissolve in 40 seconds or less, often in about 20 seconds. Finally, the content of the matrix, both in terms of direct versus nondirect compression materials, as well as the percentage of disintegrants used in accordance with the Cousins et al. formulation, were considerably higher, adding to the unpleasant gritty feel of the disintegrated formulation. The invention minimizes this and, where possible, the only grittiness is a result of the coated active material and a relatively minor percentage of other excipients.

We claim:

1. A hard, compressed, rapidly dissolvable dosage form adapted for direct oral dosing comprising: an active ingredient and a matrix including a nondirect compression filler and a lubricant, said dosage form being adapted to rapidly dissolve in the mouth of a patient and thereby liberate said active ingredient, and having a friability of about 2% or less when tested according to the U.S.P.

* * * * *

UNITED STATES PATENT AND TRADEMARK OFFICE
CERTIFICATE OF CORRECTION

PATENT NO. : 6,221,392 B1
DATED : April 24, 2001
INVENTOR(S) : Khankari et al.

It is certified that error appears in the above-identified patent and that said Letters Patent is hereby corrected as shown below:

Column 1,
Line 67, "require" should read -- requires --.

Column 2,
Line 30, "The particle would the" should read -- The particle would include the --.

Column 3,
Line 4, "that there more than" should read -- that there are more than --.
Line 41, "patients mouth" should read -- patient's mouth --.

Column 6,
Line 44, "(drug an coating)" should read -- (drug and coating) --.

Column 9,
Line 30, "are" should read -- is --.

Column 12,
Line 41, "higher that the" should read -- higher than the --.

Column 14,
Line 62, "couple evolve" should read -- couple evolves --.

Column 16,
Line 16, "lubricant were" should read -- lubricant, was --.
Line 42, "and are" should read -- and were --.

UNITED STATES PATENT AND TRADEMARK OFFICE
CERTIFICATE OF CORRECTION

PATENT NO. : 6,221,392 B1
DATED : April 24, 2001
INVENTOR(S) : Khankari et al.

It is certified that error appears in the above-identified patent and that said Letters Patent is hereby corrected as shown below:

Column 19,
Line 40, "These tablets produced" should read -- These tablets were produced --.

Signed and Sealed this

Eighth Day of January, 2002

Attest:

Attesting Officer

JAMES E. ROGAN
Director of the United States Patent and Trademark Office

Disclaimer

6,221,392—Rajendra K. Khankari, Maple Grove; John Hontz, Plymouth; Sara J. Chastain, Maple Grove; Leo Katzner, Eden Prairie, all of MN. RAPIDLY DISSOLVING ROBUST DOSAGE FORM. Patent dated Apr. 24, 2001. Disclaimer filed Apr. 25, 2006, by the assignee, Cima Labs Inc.

The term of this patent, subsequent to the term of patent number 6,024,981 has been disclaimed.

(*Official Gazette December 25, 2007*)

(12) INTER PARTES REEXAMINATION CERTIFICATE (697th)
United States Patent
Khankari et al.

(10) Number: US 6,221,392 C1
(45) Certificate Issued: Sep. 20, 2013

(54) RAPIDLY DISSOLVING ROBUST DOSAGE FORM

(75) Inventors: Rajendra K. Khankari, Maple Grove, MN (US); John Hontz, Plymouth, MN (US); Sara J. Chastain, Maple Grove, MN (US); Leo Katzner, Eden Prairie, MN (US)

(73) Assignee: Cima Labs Inc., Eden Prairie, MN (US)

Reexamination Request:
No. 95/000,160, Jul. 28, 2006

Reexamination Certificate for:
Patent No.: 6,221,392
Issued: Apr. 24, 2001
Appl. No.: 09/464,882
Filed: Dec. 16, 1999

Certificate of Correction issued Jan. 8, 2002

Related U.S. Application Data

(63) Continuation of application No. 09/388,803, filed on Sep. 2, 1999, now abandoned, which is a continuation of application No. 09/057,884, filed on Apr. 9, 1998, now Pat. No. 6,024,981.

(60) Provisional application No. 60/043,242, filed on Apr. 16, 1997.

(51) Int. Cl.
*A61K 9/00* (2006.01)
*A61K 9/46* (2006.01)
*A61K 9/20* (2006.01)

(52) U.S. Cl.
USPC ........... 424/464; 424/435; 424/441; 424/465; 424/469; 424/484

(58) Field of Classification Search
None
See application file for complete search history.

(56) References Cited

To view the complete listing of prior art documents cited during the proceeding for Reexamination Control Number 95/000,160, please refer to the USPTO's public Patent Application Information Retrieval (PAIR) system under the Display References tab.

*Primary Examiner* — Evelyn Huang

(57) ABSTRACT

The invention is directed to a hard tablet that can be stored, packaged and processed in bulk. Yet the tablet dissolves rapidly in the mouth of the patient with a minimum of grit. The tablet is created from an active ingredient mixed into a matrix of a nondirect compression filler and a relatively high lubricant content.

INTER PARTES REEXAMINATION CERTIFICATE ISSUED UNDER 35 U.S.C. 316

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is cancelled.

New claims 2-20 are added and determined to be patentable.

2. *A hard, compressed, rapidly dissolvable tablet adapted for direct oral dosing comprising: an active ingredient; a nondirect compression sugar or nondirect compression sugar alcohol; a wicking agent selected from the group consisting of microcrystalline cellulose, croscarmelose sodium, crosslinked polyvinylpyrrolidone, starches, modified starches, gums and hydroxyalkyl celluloses; a glidant; and a hydrophobic lubricant in an amount of about 1 to about 2.5% by weight, said tablet being adapted to rapidly dissolve in the mouth of a patient and thereby liberate said active ingredient, and having a friability of about 2% or less when tested according to the U.S.P., said tablet having a hardness of at least about 15 Newtons.*

3. *A hard, compressed, rapidly dissolvable tablet comprising: an active ingredient in an amount of between greater than zero and about 80% by weight of said tablet; a matrix including a nondirect compression sugar or sugar alcohol in an amount of between about 25 and about 90% by weight of the tablet and a wicking agent selected from the group consisting of microcrystalline cellulose, croscarmelose sodium, crosslinked polyvinylpyrrolidone, starches, modified starches, gums, and hydroxyalkyl celluloses; a glidant; and a hydrophobic lubricant in an amount of about 1-2.5% or more by weight, said tablet being adapted to rapidly dissolve in the mouth of a patient sufficiently to allow ingestion in 90 seconds or less and having a friability of about 2% or less when tested according to the U.S.P., said tablet having a hardness of about 20 to 50 Newtons.*

4. *A hard, compressed, rapidly dissolvable tablet comprising: an active ingredient in an amount of between greater than zero and about 80% by weight of said tablet; a nondirect compression sugar or sugar alcohol in an amount of between about 25% and about 90% by weight of said tablet; a wicking agent selected from the group consisting of microcrystalline cellulose, croscarmelose sodium, crosslinked polyvinylpyrrolidone, starches and modified starches, gums and hydroxyalkyl celluloses; and a hydrophobic lubricant in an amount of about 1.5% or more by weight, said tablet being adapted to rapidly dissolve in the mouth of a patient sufficiently to allow ingestion in 60 seconds or less and having a friability of about 1% or less when tested according to the U.S.P., and a hardness of about 15 to about 50 Newtons.*

5. *A hard, compressed, rapidly dissolvable tablet comprising: an active ingredient in an amount of between greater than zero and about 80% by weight of said tablet; a matrix including a nondirect compression sugar or sugar alcohol in an amount of between about 25% and about 90% by weight of the tablet and a wicking agent selected from the group consisting of microcrystalline cellulose, croscarmelose sodium, crosslinked polyvinylpyrrolidone, starches, modified starches, gums, and hydroxyalkyl celluloses; a glidant; and a hydrophobic lubricant, said tablet being adapted to rapidly dissolve in the mouth of a patient sufficiently to allow ingestion in 90 seconds or less and and having a friability of about 1% or less when tested according to the U.S.P., said tablet having a hardness of about 15 to 50 Newtons.*

6. *The tablet according to any one of claims 2, 3, 4 and 5, further comprising an openable and reclosable multi-tablet bottle, said tablet being stored inside said container.*

7. *The tablet according to any one of claims 2, 3, 4, and 5, wherein said nondirect compression sugar or sugar alcohol is selected from the group consisting of dextrose, mannitol, sorbitol, lactose, and sucrose.*

8. *The tablet according to claim 6, wherein said nondirect compression sugar or sugar alcohol is selected from the group consisting of dextrose, mannitol, sorbitol, lactose, and sucrose.*

9. *The dosage form according to any one of claims 2, 3, 4, and 5, wherein said non-direct compression filler in addition has a particle size which is less than 90% over 200 microns.*

10. *The dosage form according to any one of claims 2, 3, 4, and 5, wherein said active ingredient is a pharmaceutical ingredient.*

11. *The dosage form as claimed in claim 10, wherein said pharmaceutical ingredient includes at least one of antacids, analgesics, anti-inflammatories, antipyretics, antibiotics, antimicrobials, laxatives, anorexics, antihistamines, antiasthamatics, antidiuretics, antiflatuents, antimigraine agents, antispasmodics, sedatives, antihyperactives, antihypertensives, tranquilizers, decongestants, beta blockers, and combinations thereof.*

12. *The dosage form as claimed in claim 10, wherein said active ingredient is provided as a coated particle.*

13. *The dosage form as claimed in claim 12, wherein said particles are rapid release particles.*

14. *The dosage form as claimed in claim 12, wherein said particles are sustained release particles.*

15. *A plurality of hard, compressed, rapidly dissolvable tablets adapted for direct oral dosing each comprising: an active ingredient and a matrix including a non-direct compression filler and a lubricant, said tablets, said tablets being adapted to rapidly dissolve in the mouth of a patient sufficiently to allow ingestion in 90 seconds or less, and having a friability of about 1% or less when tested according to the U.S.P., said tablets being directly compressed to a hardness of at least about 15 Newtons.*

16. *A plurality of hard, compressed, rapidly dissolvable tablets adapted for direct oral dosing each comprising: an active ingredient, a non-direct compression sugar or sugar alcohol, and a lubricant in an amount of at least about 1.5% by weight, being adapted to rapidly dissolve in the mouth of a patient sufficiently to allow ingestion in 90 seconds or less and, having a friability of about 2% or less when tested according to the U.S.P., said tablets having a hardness of at least about 15 Newtons, and are capable of being stored in bulk after being directly compressed and prior to being packaged; said plurality of tablets being packaged in an openable and reclosable package.*

17. *The dosage form according to claim 16, wherein said dosage forms have a friability of about 1% or less when tested according to the U.S.P.*

18. *The dosage form according to claim 15, wherein said non-direct compression filler is a sugar or sugar alcohol.*

19. *The dosage form according to claim 15 or 16, having a hardness of about 15 to about 50 Newtons.*

20. *The dosage form according to claim 15, wherein said package is an openable and reclosable multi-tablet bottle.*

* * * * *